(12) United States Patent
Mehrotra et al.

(10) Patent No.: US 10,091,468 B2
(45) Date of Patent: Oct. 2, 2018

(54) SYSTEM AND METHOD FOR TRACKING CONTENT IN A MEDICINE CONTAINER

(71) Applicant: Northwestern University, Evanston, IL (US)

(72) Inventors: Sanjay Mehrotra, Winnetka, IL (US); Fatma Seda Memik, Evanston, IL (US); Ilya Mikhelson, Wilmette, IL (US)

(73) Assignee: Northwestern University, Evanston, IL (US)

( * ) Notice: Subject to any disclaimer, the term of this patent is extended or adjusted under 35 U.S.C. 154(b) by 279 days.

(21) Appl. No.: 14/995,653

(22) Filed: Jan. 14, 2016

(65) Prior Publication Data

US 2016/0212389 A1    Jul. 21, 2016

Related U.S. Application Data

(60) Provisional application No. 62/105,966, filed on Jan. 21, 2015.

(51) Int. Cl.
| | |
|---|---|
| *H04N 7/00* | (2011.01) |
| *H04N 7/18* | (2006.01) |
| *A61J 7/04* | (2006.01) |
| *G06F 19/00* | (2018.01) |
| *A61J 1/14* | (2006.01) |

(52) U.S. Cl.
CPC ............ *H04N 7/188* (2013.01); *A61J 1/1418* (2015.05); *A61J 7/04* (2013.01); *G06F 19/3418* (2013.01); *G06F 19/3462* (2013.01); *A61J 2200/30* (2013.01); *A61J 2200/74* (2013.01)

(58) Field of Classification Search
CPC .... A61J 7/04; A61J 7/02; A61J 7/0409; A61J 7/0481; A61J 2200/30; A61J 2200/76; A61J 2200/74; A61J 2200/70; A61J 7/0418; G06F 19/3462; G06Q 10/10; F04C 2270/0421
See application file for complete search history.

(56) References Cited

U.S. PATENT DOCUMENTS

| | | | |
|---|---|---|---|
| 4,419,016 A | 12/1983 | Zoltan | |
| 6,604,650 B2 | 8/2003 | Sagar | |
| 7,081,807 B2 | 7/2006 | Lai | |
| 7,269,476 B2 | 9/2007 | Ratnakar | |
| D592,507 S | 5/2009 | Wachman et al. | |
| 7,907,477 B2 * | 3/2011 | Puzia | ............... A61J 7/0472 215/230 |

(Continued)

FOREIGN PATENT DOCUMENTS

WO      2013126897 A1    8/2013

*Primary Examiner* — Frank Huang
(74) *Attorney, Agent, or Firm* — Benesch, Friedlander, Coplan & Aronoff LLP

(57) ABSTRACT

A system and a method include a medicine container having a bottle and a cap. The medicine container includes a controller and can include a camera located in the cap. The container can include a scale in the base. The controller controls the camera to take an image of the inside of the container to detect the contents, along with a weight measurement to determine usage of the content. A memory connects with the camera and the scale to store the image and weight data. The container can communicate data with a backend server using a wired or wireless connection upon a trigger event. Multiple containers can be connected to form a network of containers.

21 Claims, 4 Drawing Sheets

(56) References Cited

U.S. PATENT DOCUMENTS

| | | | |
|---|---|---|---|
| 8,417,090 B2* | 4/2013 | Fleming | H04N 5/77 386/226 |
| 8,457,879 B2* | 6/2013 | Merkel | G01C 21/20 340/541 |
| 8,754,759 B2 | 6/2014 | Stein et al. | |
| 2003/0078696 A1* | 4/2003 | Sakamoto | A63H 3/52 700/245 |
| 2005/0237187 A1* | 10/2005 | Martin | G08B 13/19645 340/541 |
| 2006/0268108 A1* | 11/2006 | Abraham | G08B 13/1968 348/143 |
| 2007/0016443 A1* | 1/2007 | Wachman | G06F 19/3456 705/2 |
| 2007/0153091 A1* | 7/2007 | Watlington | H04N 7/15 348/208.14 |
| 2008/0273754 A1* | 11/2008 | Hick | G06K 9/00771 382/103 |
| 2009/0077167 A1* | 3/2009 | Baum | G06F 17/30017 709/203 |
| 2009/0122144 A1* | 5/2009 | Latham | G08B 13/19632 348/155 |
| 2009/0195655 A1* | 8/2009 | Pandey | G08B 13/19647 348/158 |
| 2010/0128123 A1* | 5/2010 | DiPoala | G08B 13/19619 348/143 |
| 2010/0270257 A1* | 10/2010 | Wachman | G06F 19/3462 215/228 |
| 2010/0312734 A1* | 12/2010 | Widrow | G06K 9/6247 706/25 |
| 2011/0055747 A1* | 3/2011 | Hua | G06F 1/1632 715/771 |
| 2011/0181716 A1* | 7/2011 | McLeod | H04N 7/181 348/143 |
| 2012/0323364 A1* | 12/2012 | Birkenbach | G06F 3/014 700/257 |
| 2014/0240094 A1 | 8/2014 | Stein et al. | |

* cited by examiner

SYSTEM AND METHOD FOR TRACKING CONTENT IN A MEDICINE CONTAINER

CROSS-REFERENCE TO RELATED APPLICATION

This application claims the benefit of U.S. Provisional Application Ser. No. 62/105,966, filed Jan. 21, 2015, which is incorporated in its entirety herein.

BACKGROUND

Some solutions have been proposed for tracking and/or motivating usage from medicines containers including medication bottles and trays. One product produces a glowing light alert to remind patients to take medication at specific intervals. The product communicates with a home base station and use may be limited outside a controlled environment of the home base station. There are also various electronic pill dispenser systems that require a special medication tray to be programmed to create a reminder alert periodically and dispense one pill at a time. The trays cannot be used for liquids.

DESCRIPTION

Tracking the usage of contents in a container, e.g., one in which medication is delivered, can be useful. The embodiments include a circuit that is capable of taking, storing, and transmitting such information upon registering cap opening and closing events. The embodiments are capable of automatically collecting usage information of the container while meeting form factor requirements. The embodiments do not require continuous communication with a home base, making the container portable.

Figure 1:
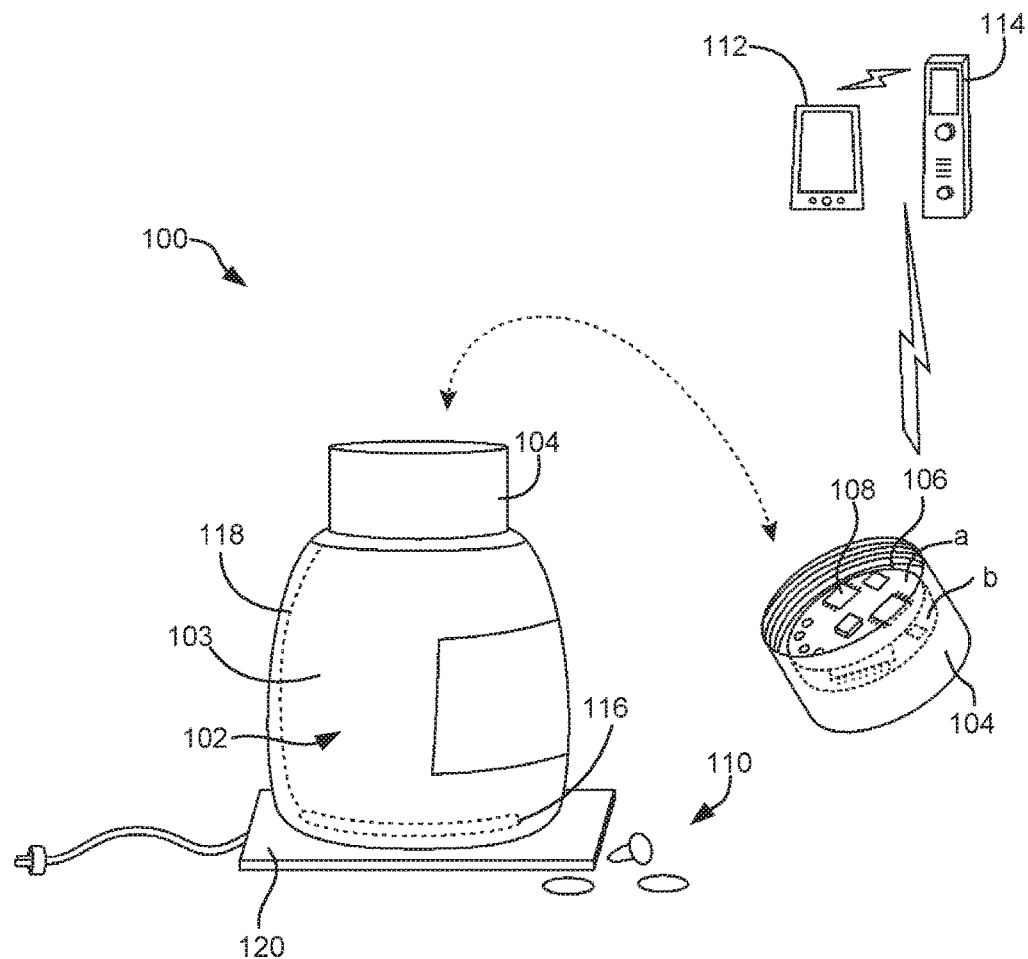
FIG. 1 is a diagram of an example medicine container.

FIG. 1 is a diagram of an example container 100, e.g., a medicine container. The container 100 can include a bottle, a tray, etc. for containing medicine. For sake of explanation, in one example the container 100 can include a bottle 102 portion and a cap 104 portion. The bottle 102 can be implemented with a tray or other type of container and the cap 104 can be implemented as a lid, for example. In one example, the bottle includes a wall 103. The cap 104 is shown positioned on and off the bottle 102. Within the cap 104 is positioned a circuit 106 including circuit components 108. The circuit 106 can include one or more separate layers, e.g., layers a and b. For example, the circuit 106 can include a multi-board, two-layer printed circuit board (PCB) design to fit within the cap 104.

The container 100 can be used for holding content 110, e.g., medicaments. The content 110 can exist in different forms, e.g., pills, liquid, etc. The circuit components 108 can communicate information about the contents, e.g., to a server 114 or a communication device 112, e.g., a smartphone, a tablet, a computer, an access point, a router, etc. The container 100 can include a scale 116. The scale 116 can be positioned at a bottom of the container 100, for example, for measuring the content 110. The scale 116 can be wirelessly connected to the cap 104, and/or connected by a wire 118, e.g., a flat-flex cable routed through the wall 103 of the container 100. The wire 118 can also connect with a charging station 120, e.g., for recharging the circuit components 108 of the cap 104. Additionally or alternatively, the container 100 can be charged wirelessly.

Figure 2:
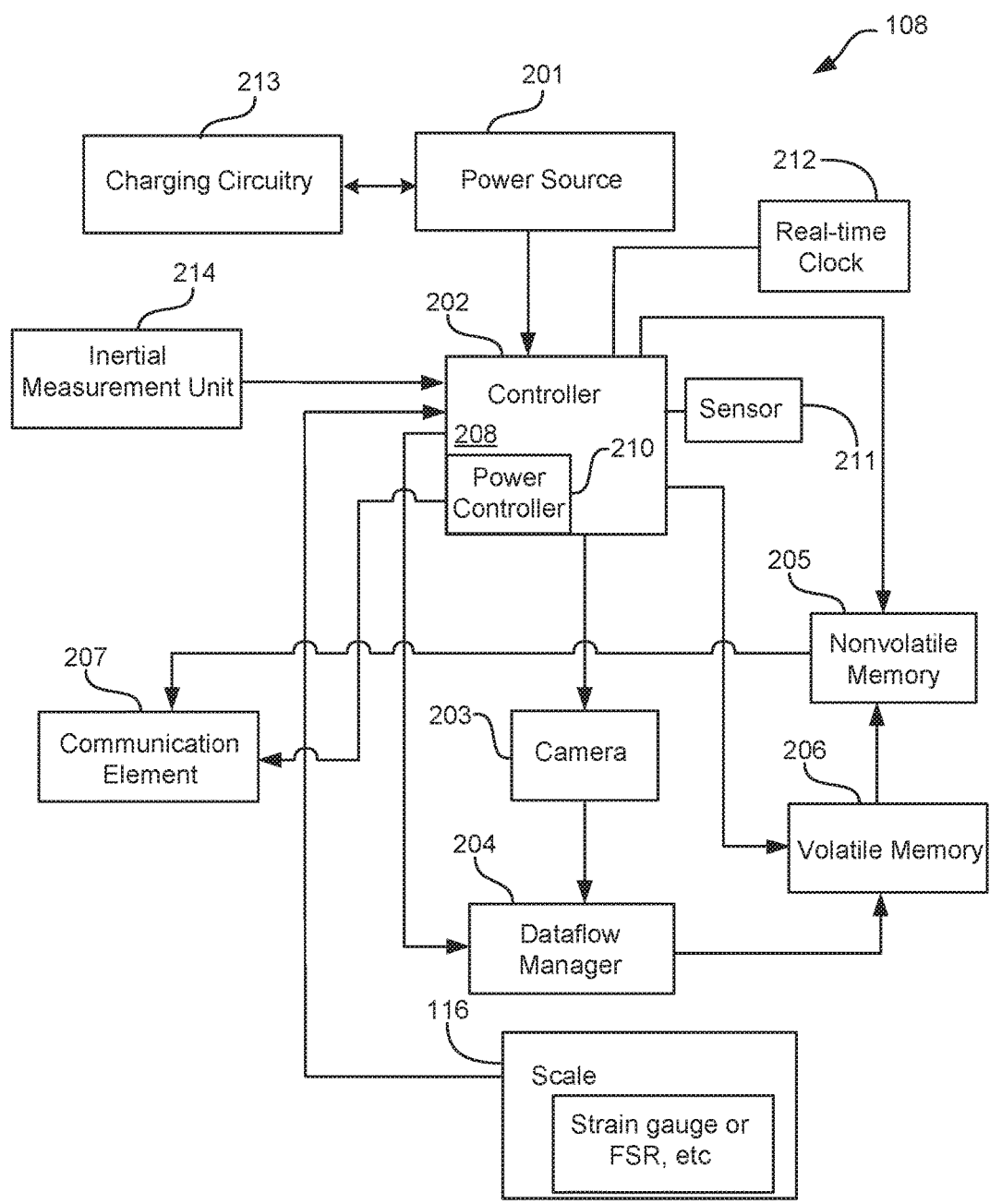
FIG. 2 is a block diagram of example circuit components for tracking the contents of the medicine container.

FIG. 2 is a block diagram of example circuit components 108 for tracking the contents 110 of the container 100. The circuit components 108 can include a camera 203, a controller circuit 202, a dataflow manager 204, a volatile memory 206, a nonvolatile memory 205, a communication element 207, a power source 201, a scale 116, a sensor 211, a real-time clock 212, a charging circuitry 213, and an inertial measurement unit 214 as well as other peripherals, etc. The inertial measurement unit 214 can include an accelerometer and a gyroscope, etc. More or less than the illustrated components can be used, e.g., based on an implementation. For example, in some implementations, the dataflow manager 204 and the volatile memory 106 are not included, and the controller 202 connects with the nonvolatile memory 205. While illustrated in the cap 104, the circuit components 108 can be located in the cap 104, the bottle 102, or both the cap 104 and the bottle 102.

The camera 203, or other image sensor, can be positioned to view the content 110 of the bottle 102 and take a picture of the content 110 a determined time period after the sensor 211 is triggered. The camera 203 can produce an image that includes one or more of a video or a photo, etc., in greyscale, black and white, color and infrared (IR), etc., depending on an implementation, power constraints, etc. The sensor 211 can determine, for example by measuring forces on the cap 104, when the cap 104 is opened from the bottle 102 and replaced on the bottle 102. An example of a mechanism to identify cap opening and closing events is a pushbutton that is depressed when the cap is closed, triggering cap closed event, and released, triggering cap removal event, when the cap is opened. The opening and closing of the cap 104 can generate an interrupt for the controller 202, which triggers the controller 202 to perform further actions, e.g., image capturing, time capturing, weight capturing, circuit wakeup and sleep, communications, etc., as described in more detail below. The controller 202 can process position information received from the inertial measurement unit 214 to ensure that the container is located in a determined position, e.g., upright, before instructing the scale 116 to take a weight measurement, or before the weight measurement sent to the controller 202 by the scale 116 is considered. The controller 202 can also be programmed to take actions on a pre-specified schedule.

The time period after the controller 202 determines that the sensor 211 detects the cap 102 has been place on the bottle 102, the controller 202 activates the camera 203 to take a picture of the content 110. The dataflow manager 204 if there is one can buffer the image from the camera 203 into the volatile memory 206. The image is then transferred to the non-volatile memory 205. Additionally, weight information regarding the content 110 and a timestamp of the weighing, e.g., as determined by the scale 116 located at a bottom of the bottle 102 and the real-time clock 212, can also be stored in the nonvolatile memory 205. If there is no dataflow manager 204, when the controller 202 receives the image, weight and timestamp information, the controller 202 transfers the information to non-volatile memory 205. Once the controller 202 establishes a connection, e.g., either wired or wirelessly, the communication element 207 can send the image data and weight information, and the timestamp to the communication device 112 and/or the server 114.

To conserve power from the power source 201, the container 100 can be normally in a low-power state. For example, the only component that is powered is the controller 202, which itself is in a deep sleep waiting for a triggering event. The controller 202 can initiate other components, e.g., camera 203, communication element 207, volatile memory 206, non-volatile memory 205, etc. to enter stand-by, low power or sleep states, battery recharging, etc.

Once the event occurs, e.g., opening of the 104 cap, the controller 202 can power the other devices. When the cap 104 is closed, a picture is taken to capture an image. A light emitting diode (LED) or other flash can be used to illuminate dark conditions. The image is transferred through the dataflow manager 204 to the volatile memory 206. Once the transfer of image, weight, and other usage related information to the volatile memory 206 is complete, the information can be transferred from volatile memory 206 to the non-volatile memory 205. The information can be stored in the nonvolatile memory until a connection is available. The container 100 is put to sleep until a communication channel is established, or a new event, e.g. reopening of the cap 104, is triggered. In one example, while in sleep mode the battery can be recharged.

A power controller 210 can monitor the system for various system events. At various times the power controller 210 wakes up the desired components to properly respond to the events. If the event concerns the availability of a communication link to upload the buffered information in the nonvolatile memory 205, then memory device and the communication element 207 are activated and information transfer is performed. If the event concerns the opening or closing of the cap 104, the power controller 210 wakes up the sequence of components to perform the desired tasks, e.g., capture and store an image, time stamp the event, etc. The power controller 210 puts those components which are no longer needed back to sleep or into another low power state.

In one embodiment, the controller 202 includes a microcontroller, the nonvolatile memory 205 includes a Flash Memory, the volatile memory 206 includes a Static Random Access Memory Integrated Circuit (SRAM IC), the communication element 207 includes a Bluetooth System On Chip (SoC), the camera 203 includes a complementary metal oxide semiconductor (CMOS) camera, the dataflow manager 204 includes a Complex Programmable Logic Device (CPLD), the scale 116 can include a strain gauge or a force-sensitive resistor (FSR), etc., and the power source 201 includes a rechargeable battery, e.g., a Lithium-Polymer battery. The circuit 106 can implement a system-on-board designed to manage, process and/or analyze data produced by the image sensor. A customized memory controller can be implemented in the CPLD. The CPLD coordinates high speed data movement between the image sensor and the storage buffer.

In the multi-layer board configuration, the bottle facing layer can include the camera 203, controller 202, dataflow manager 204, volatile memory 206, and non-volatile memory 205. The cap facing layer can include the communication element 207, power source 201, and peripheral circuit elements, e.g., voltage regulators. An interface between the two layers a, b in the form of a connector, e.g., a 12 pin connector, electrically connects the two layers a, b, to allow for the transmission of data and power, etc. between the two layers a, b. The layers can utilize both sides of the PCBs for components.

Figure 3:
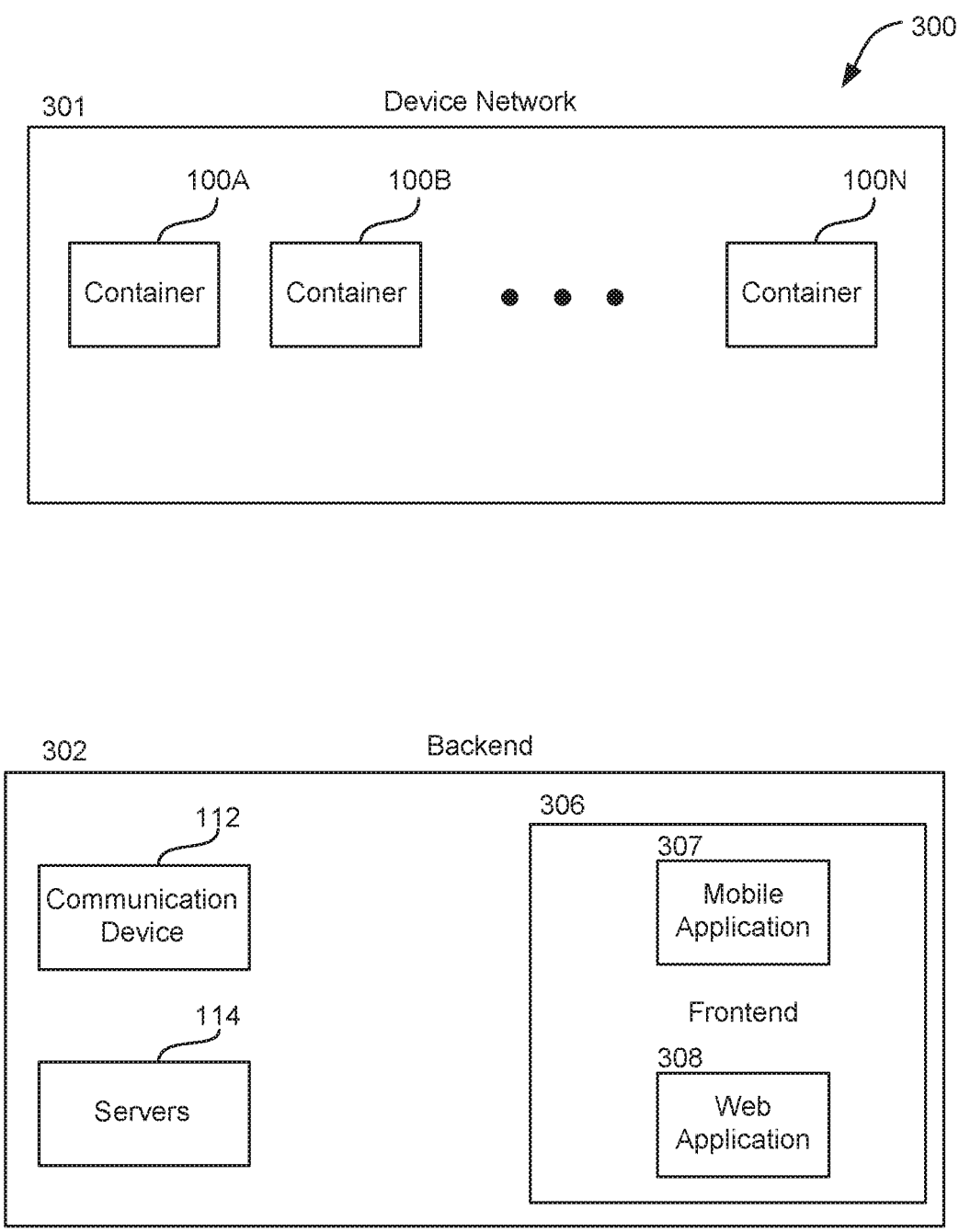
FIG. 3 is a block diagram of an example system for transferring image, weight and other data to and/or from the medicine container.

FIG. 3 is a block diagram of an example system 300 for transferring image, weight and other data to and/or from the containers 100A-N. The physical system can include two levels, e.g., a device network 301 and the backend 302. The device network 301 can include multiple containers 100A-N, or other smart bottles, smart trays, etc. Information can be conveyed between containers 100A-N, between the device network 301 and the backend 302, and/or between the communication device 112, servers 114, etc. on the backend 302, using wired and/or wireless communication, e.g., Bluetooth, Wi-Fi, cellular, e.g., 3G/4G, universal serial bus (USB), Ethernet, etc.

The device network 301 includes containers 100A-100N, e.g., the bottle 102 with the removable cap 104 described herein. The containers 100A-N can communicate with each other wirelessly and/or by wire. The containers 100A-N can also communicate with an external device, e.g., communication device 112, including a smart phone, a laptop, a tablet, a computer, a router, etc. The backend 302 includes communication device 112, a wide area network (WAN), e.g., the Internet, local area networks (LANs), and/or servers 114, etc. In one implementation, the information from the containers 100A-N is forwarded to the communication device 112, which then sends the information to the servers 114 using Bluetooth, Wi-Fi, 3G/4G, USB, Ethernet, etc. Additionally or alternatively, the containers 100A-N can send the information directly to the servers 114 using Bluetooth, Wi-Fi, 3G/4G, USB, Ethernet, etc.

When the container 100A-N is opened and closed, and a picture is taken and the weight measured, the image and weight information are ready for processing. When the container 100A-N is able to establish a connection with the backend 302, then the captured information can be forwarded and further analyzed at the backend 302. Relevant information can then be sent back to the container 100A-N for further action. For example, if the weight has not changed sufficiently, an alert could be issued to the user indicating that he has forgotten to take the medication. Alternatively, if the bottle contained one content, but now contains another, the user can be notified that the wrong content may be contained in the bottle, or the cap placed on the wrong bottle and/or mixed up his pills. Such notifications could be delivered via the communication device 112, and/or via feedback mechanisms, e.g. lights, vibration, sound, etc. located on the container 100A-N itself.

If a connection cannot be established, the image and weight information, along with a timestamp, is buffered on the container 100A-N until a connection is established. In one example, there is enough memory to last a duration of the prescription. During the disconnected state, the container 100A-N can still issue reminders and alerts, e.g., using a built-in clock. At the backend 302, servers 114, images, weights, and corresponding timestamps can be stored in a database for each user. This information is made available, e.g., through a website application 308 of the frontend 306. For a patient or caregiver, information can be available for individual persons. For a doctor, information can be available for all of his patients. For a pharmacy, relevant information can be available for their clients. The information can also be available to users through the communication device 112, e.g., in the form of an application 307. The application 307 can be used to monitor information like the website application 308, and can also issue alerts and notifications like the container 100A-N. This adds redundancy to both systems to help maximize a probability of adherence to the medication regimen.

Therefore, the systems and methods described herein can help assure adherence with as little burden as possible. For example, if the user switches caps on pill bottles or pills are put in different containers within a set of container trays, etc., the system can automatically adjust to maintain the medication regimen seamlessly. Additionally or alternatively, upon getting a refill of a medication, or a new medication altogether, the user does not have to worry about which bottle he places the new pills in. The camera 203 enables the system to recognize the true contents, and the regimen assigned to that cap 104 gets updated to reflect the contents of the bottle 102. The user does not have to switch the caps 104 back, as the system can be self-adjusting. The containers 100A-N can be battery operated, with enough battery life to insure that no battery change has to be provided for a duration of a given medication's prescription, e.g., before a refill, when the battery can be changed by the pharmacy. Additionally or alternatively, the battery can be rechargeable, e.g., with charging circuitry 213 integrated in to the container 100. The charging circuitry 213 can connect with a power source using wired and/or wireless connections, e.g., a USB and/or a wireless charging platform. If no connection can be established for information transfer, the information is buffered, e.g., by the nonvolatile memory 205, until the connection can be established again. The transmission and other hardware is embedded in the container 100A-N, so the system is portable, and it does not rely on any peripherals for operation.

Figure 4:
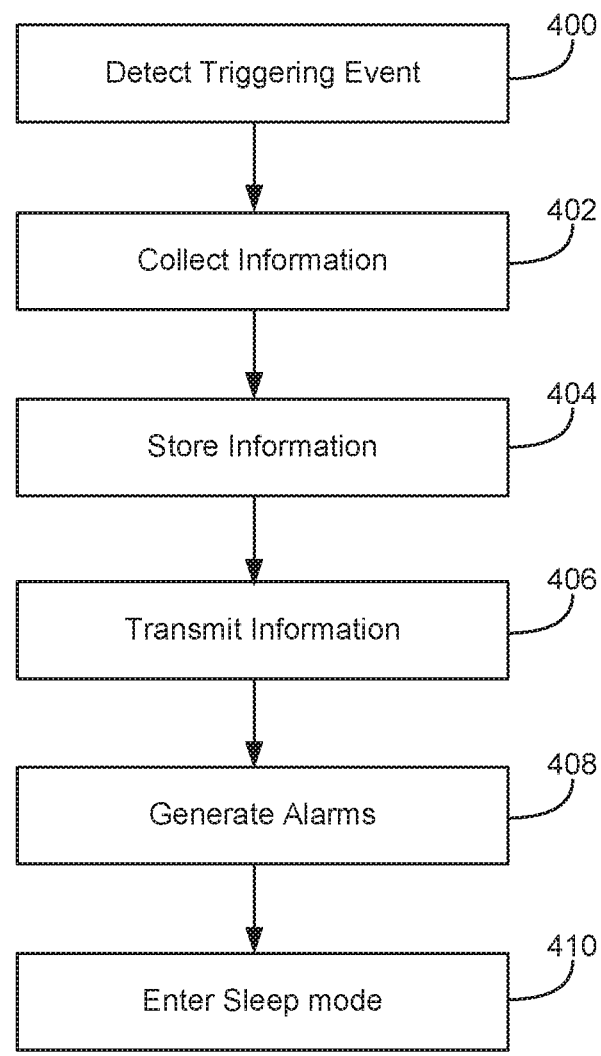
FIG. 4 is a flowchart of an example process for using the medicine container.

FIG. 4 is a flowchart of an example process for using the container 100. The process includes the circuit 106 that can be used to track a bottle usage based on the trigger events, e.g., open/close events. The circuit 106 can be sized to fit a standard bottle cap used to dispense medication from a pharmacy. Upon detecting a trigger event, the circuit 106 generates a signature with information, e.g., that the triggering event occurred, a time that the triggering event occurred, a weight of the content 110 of the bottle 102, an image of the content 110 of the bottle, etc. (400). The information is collected, e.g., image information from the camera 203, weight information from the scale 116, time stamp information from the controller 202, etc. (402). The controller can be connected with a clock and/or counter to determine the time stamp information.

One example of the trigger event is that the container 100 is opened or closed. Upon the detection of cap closed event, the camera 203 is activated to capture the image of the bottle content 110 as observed from its view. The image can be first stored in an image buffer, e.g., the volatile memory 206, and then transferred to a non-volatile memory 205 (404). Then, the communication element 207, e.g. Bluetooth, Wi-Fi, 3G/4G, USB, Ethernet, etc., searches for the communication device 112, e.g., smartphone, tablet, computer, etc. If the communication element 207 does not find a device within range, the search can be stopped. The search can be reinitiated on a periodic basis, e.g., every 10 minutes. When a connection is established between the bottle 102 and the communication device 112, the communication element 207 transmits the stored information to the communication device 112 (406). Transmitted information includes a source identifier, a time stamp, the image, the weight, etc. The communication device 112 can then forward the information to the server 114. Additionally or alternatively, the container 100 can directly forward the information to the server 114. The server 114 can store the incoming data organized according to the transmitted information, e.g., source, time, and images, etc. This data can then be accessed for further record keeping and/or analysis.

The circuit can operate in two modes: (i) non-networked and (ii) networked. In the non-networked mode the container 100 does not communicate with a secondary unit. In the networked mode, information can be sent to the communication device 112, e.g., smartphone, laptop, etc., after the communication element 207 establishes a secure connection. The communication device 112 may be programmed to process the received data itself, and/or the communication device 112 may forward the acquired data to the server 114. In either the non-networked or networked mode, a buzzer or LED can used to create an auditory or visual alarm when a trigger event has not occurred for a determined amount of time (408). The alarm can be programmed into the controller 202 based on a determined expected frequency of access to the medication inside the pill bottle. Alarms can be generated through sound, light, and/or a message sent to a known destination, e.g., the user's smartphone, tablet, computer, etc.

The container 100 can be kept in a sleep state until there is an interrupt, e.g., detected opening or closing of the cap 104 (410). In the sleep state, all unnecessary powered elements can be shut off when not in use. For example, each subsystem is turned on only for its necessary operation, e.g., the camera 203 and volatile memory 206 is turned on to take and buffer an image. Then, the camera 203 turns off while the image is stored in non-volatile memory 205. Subsequently, the volatile memory 206 turns off and the communication element 207 turns on to transfer the image. Followed by the communication element 207 turning off and the controller 202 going into sleep mode, only waking up for an external trigger, e.g., the cap removal event. The cap removal event can be detected, for example, by a Hall sensor 211. Power management can be regulated by the controller 202 through a power-gating approach.

The systems and methods described above may be implemented in many different ways in many different combinations of hardware, software firmware, or any combination thereof. In one example, the systems and methods can be implemented with a processor and a memory, where the memory stores instructions, which when executed by the processor, causes the processor to perform the systems and methods. The processor may mean any type of circuit such as, but not limited to, a microprocessor, a microcontroller, a graphics processor, a digital signal processor, or another processor. The processor may also be implemented with discrete logic or components, or a combination of other types of analog or digital circuitry, combined on a single integrated circuit or distributed among multiple integrated circuits. All or part of the logic described above may be implemented as instructions for execution by the processor, controller, or other processing device and may be stored in a tangible or non-transitory machine-readable or computer-readable medium such as flash memory, random access memory (RAM) or read only memory (ROM), erasable programmable read only memory (EPROM) or other machine-readable medium such as a compact disc read only memory (CDROM), or magnetic or optical disk. A product, such as a computer program product, may include a storage medium and computer readable instructions stored on the medium, which when executed in an endpoint, computer system, or other device, cause the device to perform operations according to any of the description above. The memory can be implemented with one or more hard drives, and/or one or more drives that handle removable media, such as diskettes, compact disks (CDs), digital video disks (DVDs), flash memory keys, and other removable media.

The processing capability of the system may be distributed among multiple system components, such as among multiple processors and memories, optionally including multiple distributed processing systems. Parameters, databases, and other data structures may be separately stored and managed, may be incorporated into a single memory or database, may be logically and physically organized in many different ways, and may be implemented in many ways, including data structures such as linked lists, hash tables, or implicit storage mechanisms. Programs may be parts (e.g., subroutines) of a single program, separate programs, distributed across several memories and processors, or implemented in many different ways, such as in a library, such as a shared library (e.g., a dynamic link library (DLL)). The DLL, for example, may store code that performs any of the system processing described above.

As an example, the systems and methods can include the following components. More or less, and other, components may be used. An OV2640 camera module 203, which captures a 640×480 pixel image, controlled by an Atmel ARM microcontroller (ATSAM4S8B) 202, which also has an integrated real-time clock 212. The system can determine when the cap 104 is opened using a Hall sensor (A1202UA) 211 and magnets in the wall 103 of the bottle 102. After capture, the image can be transferred into a Macronix International Flash memory chip (MX25L3206E) 205. The Bluetooth 207, an AckME Bobcat System on a Chip (AMS001), establishes a connection with the user's communication device 112. There is also the scale 116, along with the inertial measurement unit 214 (e.g., MPU-6050). When the inertial measurement unit 214 detects that the bottle 102 is upright and stationary, a weight measurement is taken. There is charging circuitry 213, which includes a USB charging port and an inductive charging coil for wireless charging.

While various embodiments have been described, it can be apparent that many more embodiments and implementations are possible. Accordingly, the embodiments are not to be restricted.

The invention claimed is:

1. A system, comprising:
a medicine container including a bottle and a cap;
a controller located in the medicine container, the controller connected with an image sensor to capture an image of a content in the medicine container and a scale to measure a weight of the content in the medicine container, the controller configured to process the image of the content and the weight of the content contained in the bottle;
an inertial measurement unit connected with the controller, the inertial measurement unit configured to detect a position of the medicine container, the controller configured to process the position information to ensure that the container is located in an upright position before the weight measurement is considered; and
a communication element connected with the controller, the communication element to send at least one of the image of the content and the weight of the content to at least one of a communication device and a server.

2. The system of claim 1, where the communication device includes an application configured to analyze at least one of the image of the content and the weight of the content.

3. The system of claim 2, where at least one of the controller and the communication device are configured to provide an alarm based on the analysis.

4. The system of claim 1, where the controller enters a sleep mode based on the cap being closed.

5. A medicine container, comprising:
a controller;
an image sensor connected with the controller, the controller configured to control the image sensor to take an image of a content of the medicine container to detect usage of the content;
a memory connected with the image sensor, the memory configured to store the image;
a scale connected with the controller, the scale configured to measure a weight of the content of the medicine container;
an inertial measurement unit connected with the controller, the inertial measurement unit configured to detect a position of the medicine container, the controller configured to process the position information to ensure that the container is located in an upright position before the weight measurement is considered.

6. The medicine container of claim 5, further including a printed circuit board, where the controller, the image sensor and the memory are located on the printed circuit board.

7. The medicine container of claim 6, where the printed circuit is sized to fit in a bottle cap used to dispense medication.

8. The medicine container of claim 6, where the printed circuit board includes separate layers electrically connected together.

9. The medicine container of claim 5, where the memory comprises volatile memory configured to temporarily store the image and a non-volatile memory configured to store the image until communication becomes available.

10. The medicine container of claim 9, further comprising a dataflow manager connected with the controller, the dataflow manager configured to control a flow of the image from the volatile memory to the non-volatile memory.

11. The medicine container of claim 5, further including a communication element connected with the controller, the communication element configured to send the image to a communication device or a server.

12. The medicine container of claim 5, further including a power controller connected with the controller, the power controller configured to put a circuit component in sleep or low power state when not in use.

13. The medicine container of claim 12, where the power controller is further configured to turn on the circuit component when the medicine container is opened or closed.

14. A method, comprising:
detecting with a controller a cap being opened from a medicine container;
collecting image information and weight information of a content in the medicine container when the cap of the medicine container is opened; and
detecting a position of the medicine container, the controller configured to process the position information to ensure that the container is located in an upright position before the weight information is considered.

15. The method of claim 14, further comprising transmitting the information to at least one of a communication device and a server for analysis of the information.

16. The method of claim 14, further comprising:
detecting with the controller when the cap is replaced on the medicine container; and
collecting at least one of image information and weight information of the content in the medicine container when the cap is replaced on the medicine container.

17. The method of claim 16, further comprising generating an alarm based on the image information or the weight information.

18. The method of claim 16, further comprising the controller and other components entering sleep mode after detecting that the cap is replaced on the medicine container.

19. The system of claim 1, where the content comprises a liquid.

20. The medicine container of claim 5, where the content comprises a liquid.

21. The method of claim 14, where the content comprises a liquid.

\* \* \* \* \*